United States Patent [19]
Scofield

[11] Patent Number: 5,804,191
[45] Date of Patent: Sep. 8, 1998

[54] SPERM AS IMMUNOGEN CARRIERS

[76] Inventor: Virginia L. Scofield, 372 Redwood Dr., Pasadena, Calif. 91105

[21] Appl. No.: 865,724

[22] Filed: May 30, 1997

Related U.S. Application Data

[63] Continuation-in-part of Ser. No. 406,299, Mar. 17, 1995, abandoned, which is a continuation-in-part of Ser. No. 343,008, Nov. 21, 1994, abandoned.

[51] Int. Cl.$^6$ .................... A61K 39/385; A61K 45/00; A61K 9/127; G01N 33/567

[52] U.S. Cl. .................... 424/193.1; 424/278.1; 424/450; 424/489; 435/7.21; 435/325

[58] Field of Search .................... 435/7.21, 325, 435/352, 363; 424/450, 480, 184.1, 193.1, 278.1, 489

[56] References Cited

U.S. PATENT DOCUMENTS

| | | | |
|---|---|---|---|
| 4,161,519 | 7/1979 | Talwar | 424/194.1 |
| 4,744,983 | 5/1988 | Morein | 424/196.11 |

OTHER PUBLICATIONS

M. Clerici, et al., 37 Circumvention of Defective CD4 T Helper Cell Function in HIV–Infected Individuals by Stimulation with HLA Alloantigens, *The Journal of Immunology* vol. 144, No. 9, May 1, 1990, pp. 3266–3271.

J. Berzofsky et al., "Construction of Peptides Encompassing Multideterminant Clusters of Human Immunodeficiency Virus Envelope to Induce in Vitro T Cell Responses in Mice and Humans of Multiple MHC Types", *Journal of Clinical Investigation, Inc.* vol. 88, Sep. 1991, pp. 876–884.

M. Clerici et al., "Immunization with Subunit Human Immunodeficiency Virus Vaccine Generates Stronger T Helper Cell Immunity than Natural Infection", *Eur. J. Immunol.* vol. 21, 1991, pp. 1345–1349.

J. Salk et al., "A Strategy for Prophylactic Vaccination Against HIV", *Science* vol. 260, May 28, 1993, pp. 1270–1272.

B. Haynes, "Scientific and Social Issues of Human Immunodeficiency Virus Vaccine Development", *Science* vol. 260, May 28, 1993, pp. 1279–1286.

D. Long et al, "Characterization of Human Immunodeficiency Virus Type I gp120 Binding to Liposomes Containing Galactosylceramide", *Journal of Virology* Sep. 1994, pp. 5890–5898.

J. Williams, et al., "Combined Vaccines and Simultaneous Administration", *Annals of the New York Academy of Science* vol. 754, pp. 114–125, 1995.

C. Schaper et al., "Statistical Issues in The Design of HIV Vaccine Trials", pp. 1–19, Annals of the New York Academy of Sciences, vol. 754, 1995.

B. Golding et al., "Vaccine Strategies: Targeting Helper T Cell Responses", *Annals New York Academy of Sciences* pp. 126–137, vol. 754 1995.

R. Ehrdardt et al., "The Role of sIgA+ B Cells in Oral Immunity", *Annals New Your Academy of Sciences* pp. 138–141, vol. 754 1995.

C. Alving, "Liposomal Vaccines: Clinical Status and Immunological Presentation for Humoral and Cellular Immunity", *Annals New York Academy of Sciences* pp. 143–151, vol. 754, 1995.

(List continued on next page.)

*Primary Examiner*—Nancy Degen
*Assistant Examiner*—William Sandals
*Attorney, Agent, or Firm*—Knobbe, Martens, Olson & Bear, LLP

[57] ABSTRACT

Vaccine compositions, contraceptives, and gene therapy delivery vectors are disclosed in which sperm cells or components thereof are used to deliver immunogens or selected gene sequences to target cells both in vitro and in vivo. Methods of making the vaccine compositions, contraceptives, and gene therapy delivery formulations are disclosed. Methods of vaccination, contraception, and gene therapy are also disclosed.

17 Claims, 6 Drawing Sheets

OTHER PUBLICATIONS

F. Vogel, "Immunologic Adjuvants for Modern Vaccine Formulations", Annals New York Academy of Sciences pp. 153–159, vol. 754, 1995.

J. Berzofsky, "Designing Peptide Vaccines to Broaden Recognition and Enhance Potency", Annals New York Academy of Sciences pp. 162–168, vol. 754, 1995.

R. Rahgupathy et al., "Vaccines Against Fertility", Current Opinion in Immunology 1992, vol. 4, pp. 597–602.

V. Stevens, "Vaccine Delivery Systems: Potential Methods for Use in Antifertility Vaccines", AJRI pp. 176–188 (1993).

R. Aitken, "Contraceptive Vaccines", British Medical Bulletin vol. 49, No. 1, 1993, pp. 88–99.

Rand et al., "Inhibition of Fertility in Female Mice by Immunization with a B–cell epitope, the Synthetic sperm peptide, P10G", Journal of Reproductive Immunology vol. 25, 1993, pp. 89–102.

P. Primakoff, "Sperm Proteins Being Studied for Use in a Contraceptive Vaccine", AJRI 1994, vol. 31, pp. 208–210.

"A Booster for Contraceptive Vaccines", Science vol. 266, Dec. 2, 1994, pp. 1484–1486. V. Stevens (Author).

R. Naz et al., "Molecular Identities of Human Sperm Proteins That Bind Human Zona Pellucida: Nature of Sperm–Zona Interaction, Tyrosine Kinase Activity, and Involvement of FA–1", Molecular Reproduction and Development vol. 39, 1994, pp. 397–408.

U. Deshmukh et al., "Antibody Response Against Three Epitopic Domains on Human Chorionic Gonadotropin (hCG) in Woman and Rodents Immunized with a βhCG–Based Immunucontraceptive Vaccine", Journal of Clinical Immunology vol. 14, No. 3, 1994, pp. 162–168.

G. Benagiano, "The WHO Birth Control Vaccine", The FASEB Journal vol. 8, Jul. 1994, pp. 784–786.

P. Prabhakara Reddi, et al., "Production in *Eschericia coli*, Purification and immunogeniticy of Acrosomal Protein SP–10, a Candidate Contraceptive Vaccine", Gene vol. 147, 1994, pp. 189–195.

P. O'Hern et al., "Reversible Contraception in Female Baboons Immunized with a Synthetic Epitope of Sperm–Specific Lactate Dehydrogenase", Biology of Reproduction vol. 52, 1995, pp. 331–339.

P. Sparling et al., "Vaccines for Bactiral Sexually Transmitted Infections: A Realistic Goal?", Proc. Natl. Acad. Sci. USA vol. 91, Mar. 1994, pp. 2456–2463.

A. Adimora, et al., "Vaccines for Classic Sexually Transmitted Diseases", Sexually Transmitted Diseases in the AIDS ERA: Part II, vol. 8, No. 4, Dec. 1994, pp. 859–876.

C. Gibbs, Jr. et al., "Observations after Human Immunodeficiency Virus Immunization and Challenge of Human Immunodeficiency Virus Seropositive and Seronegative Chimpanzees", Proc. Natl. Acad. Sci. USA vol. 88, Apr. 1991, pp. 3348–3352.

P. Marx et al., "Protection Against Vaginal SIV Transmission with Microencapsulated Vaccine", Science vol. 260, May 28, 1993.

C. Miller, "Animal Models of Viral Sexually Transmitted Diseases", AJRI vol. 31, pp. 52–63, 1994.

B. Lohman et al., "A Partially Attenuated Simian Immunodeficiency Virus Induces Host Immunity That Correlates with Resistance to Pathogenic Virus Challenge", Jour. of Virology vol. 68, No. 11, No. 1994, pp. 7021–7029.

C. Miller et al., "Intravaginal Inoculation of Rhesus Macaques with Cell–Free Simian Immunodeficiency Virus Results in Persistent or Transient Viremia", Journal of Virology vol. 68, No. 10, pp. 6391–6400, 1994.

C. Mandell et al., "Bone Marrow Monocyte/Macrophages Are an Early Cellular Target of Pathogenic and Nonpathogenic Isolates and Simian Immunodeficiency Virus (SIVmac) in Rhesus Macaques", Laboratory Investigation vol. 72, No. 3, 1995, pp. 323–333.

R. Le Grand et al., "Infection of Macaques after vaginal exposure to a primary isolate of SIVmac251", AIDS vol. 9, No. 3, 1995, pp. 308–309.

V. Scofield, "Sperm Augmentation of HIV Infection", Grant Application, Nov. 15, 1994.

Niels Odum et al., "Homotypic Aggregation of Human Cell Lines by HLA Class–II, Class IA– and HLA–G–specific Monoclonal Antibodies", Eur. J. Immunol. vol. 21, pp. 2121–2131, 1991.

Niels Odum et al., "HLA–DR Molecules Enhance Signal Transduction Through the CD3/Ti Complex in Activated T Cells", pp. 72–77, Tissue Antigens, vol. 38, 1991.

V. Scofield et al., "Binding of Sperm to Somatic Cells Via HLA–DR", The Journal of Immunology vol. 148, No. 6, Mar. 15, 1992, pp. 1718–1724.

N. Odum et al., "MHC Class II Molecules Deliver Costimulatory Signals in Human T Cells Through a Functional Linkage with IL–2–Receptors1", Journal of Immunology vol. 150, 1993, pp. 5289–5298.

P. Akolar et al., "Bβ–Specific Activation of T Cells by the HIV Glycoprotein gp160", Scandinavian Journal of Immunology vol. 41, pp. 487–498, 1995.

D. Anderson, "Mechanisms of HIV–1 Transmission Via Semen", The Journal of NIH Research vol. 4, Jul. 1992, pp. 104–111.

"AIDS Conference in Berlin Offers Plenty of Hidden Gems", Science vol. 260, May 28, 1993, pp. 1262–1263.

V. Scofield et al., "Activation of Latent HIV by Spermatoza", IXth Intl. Conference on AIDS, Berlin Jun. 7–11, 1993.

M. Lee et al., "HIV Infection of Spermatozoa: An In Vitro Model", IXth Intl. Conference on AIDS, Berlin, Jun. 7–11, 1993.

E. Dussaix et al., "Spermatoza as Potential Carriers of HIV", Res. Virol. vol. 144, 1993, pp. 487–495.

B. Baccetti et al., "HIV–Particles in Spermatozoa of Patients with AIDS and Their Transfer into the Oocyte", The Journal of Cell Biology vol. 127, No. 4, Nov. 1994, pp. 903–914.

V. Scofield, "HIV Interaction with Sperm", AIDS vol. 8, No. 12, 1994, pp. 1733–1736.

O. Bagasra et al., "Detection of HIV–1 Proviral DNA in Sperm From HIV–1–Infected Men", AIDS vol. 8, 1994, pp. 1669–1674.

G. Nuovo et al., "HIV–1 Nucleic Acids Localize to the Spermatogonia and Their Progeny", American Journal of Pathology vol. 144, No. 6, Jun. 1994, pp. 1142–1148.

G. Milan et al., "Mechanisms of HIV/SIV Mucosal Transmission", AIDS Research Human Retroviruses vol. 10, No. 10, 1994, pp. 1305–1312.

M. Poznansky et al., "Gene Transfer into Human Lymphocytes by a Defective Human Immunodeficiency Virus Type 1 Vector", Journal of Virology vol. 65, No. 1, Jan. 1991, pp. 532–536.

M. Francolini et al., "Evidence for Nuclear Internatlization of Exogenous DNA Into Mammalian Sperm Cells", *Molecular Reproduction and Development* vol. 34, 1993, pp. 133–139.

N. Kasahara et al., "Tissue–Specific Targeting of Retroviral Vectors Through Ligand–Receptor Interactions", *Science* vol. 266, No. 25, 1994, pp. 1373–1376.

N. Allioli et al., "Use of Retroviral Vectors to Introduce and Express the β–Galactosidase Marker Gene in Cultured Primordial Germ Cells", *Development Biology* vol. 165, 1994, pp. 30–37.

Youakim, A., et al., "Overexpressing Sperm Surface β1,4–Galactosyltransferase in Transgenic Mice Affects Multiple Aspects of Sperm–Egg Interactions", *The Journal of Cell Biology* 126:1573–1583, 1994.

Lavitrano, M., et al., "The Interaction Between Exogenous DNA and Sperm Cells", *Molecular Reproduction and Development* 31:161–169, 1992.

Haimovici, F. et al., "Antifertility effects of antisperm cell–mediated immunity in mice", *Journal of Reproductive Immunology* 22:281–298, 1992.

Stover, C.K., et al., "New use of BCG for recombinant vaccines", *Nature* 351:456–460, (Jun. 1991).

Scopes, R.K., *Protein Purification* pp. 151–163, 1987 Springer Verlag N.Y.N.Y.

W.F. Paul, *Fundamental Immunol., NY Raver Press 3rd Ed.*, pp. 80–85, 402–405, 1038–1040 (1993).

Katzin, et al., *Adv. in Immunol.* 54:99–166 (1993).

S. Begler, et al., *Biology of Reproduction* 32(5):1201–1210 (1985).

V. Scofield, et al., *J. Immunol.* Vd. 148(6):1718–1724 (1992).

J. Brown, et al., *Nature* 364:33–39 (1993).

G. Shearer, et al., *Science* 262:161–162 (1993).

P. Doherty, et al., *in Vaccines, CSHL Press* pp. 1–6 (1996).

F. Brown, et al., *in Vaccines, CSHL Press* pp. xix–xx (1996).

Aitka, et al., *British Medical Bulletin* 49(1):88–89 (1993).

Francolini, et al., *Mol. Reproduction & Devel.* 34:133–139 (1993).

E.A.C. Almeida, et al., "Mouse Egg Integrin α68β1 Functions as a Sperm Receptir," *Cell* 81:1095–1104 (1995).

E.R. Ashida, et al., "Lymphocyte major histocompatibility complex–encoded class II structures may act as sperm receptors," *Proc. Natl. Acad. Sci. USA* 84:3395–3399 (1987).

C.P. Blobel, et al., "A potential fusion peptide and an integrin ligand domain in a protein active in sperm–egg fusion," *Nature* 356:248–252 (1992).

M. Clerici, et al., "T–Cell proliferation to subinfectious SIV correlates with lack of infection after challenge of macaques," *AIDS* 8:1391–1395 (1994).

R. Fuleihan, et al., "Engagement of MHC–Class II Molecules by Staphylococcal Exotoxins Delivers a Comitogenic Signal to Human B Cells," *The Journal of Immunology* 146(5):1661–1666 (1991).

W.S. Gallichan, et al., "Long–lived Cytotoxic T Lymphocyte Memory in Mucosal Tissues After Mucosal but Not Systemic Immunization," *J. Exp. Med.* 184:1879–1890 (1996).

M. Gardner, "SIV vaccines: current status," *Vaccine* 9:787–791 (1991).

T. Lehner, et al., "Genital–Associated Lymphoid Tissue in Female Non–Human Primates," *Advances in Mucosal Immunology* pp. 357–365 (1995).

B.L. Lohman, et al., "Mucosal immunization with a live, virulence–attenuated simian immunodeficiency virus (SIV) vaccine elicits antiviral cytotoxic T lymphocytes and antibodies in rhesus macaques," *J. Med. Primatol* 23:95–101 (1994).

C.J. Miller, et al., "Rhesus Macaques Previously Infected with Simian/Human Immunodeficiency Virus are Protected from Vaginal Challenge with Pathogenic SIVmac239," *Journal of Virology* 71(3):1911–1921 (1997).

E. Rubinstein, et al., "CD9, CD63, CD81, and CD82 are components of a surface tetraspan network connected to HLA–DR and VLA integrins," *Eur. J. Immunol.* 26:2657–2665 (1996).

G.M. Shearer, et al., "Vaccine strategies: selective elicitation of cellular of humoral immunity?" *Tibtech* 15:106–109 (1997).

R. Sievers–Altermann, et al., "Entry of spermatozoa into the cervical mucosa and transmission of the AIDS virus," *SAMT* 77:319 (1990).

A.I. Spira, et al., "Cellular Targets of Infection and Route of Viral Dissemination after an Intravaginal Inoculation of Simian Immunodeficiency Virus into Rhesus Macaques," *J. Exp. Med.* 183:215–225 (1996).

L.A. Thompson, et al., "The Leukocytic Reaction of the Human Uterine Cervix," *American Journal of Reproductive Immunology* 28:85–89 (1992).

J.R. Tumang, et al., "Helper T Cell–Dependent Human B Cell Differentiation Mediated by a Mycoplasmal Superantigen Bridge," *J. Exp. Med.* 171:2153–2158 (1990).

C.S. Via, et al., "T Cell–Antigen–Presenting Cell Interactions in Human Systemic Lupus Erythematosus," *The Journal of Immunology* 151(7):3914–3922 (1993).

Burton Avaccine for HIV type 1: The antibody perspective. PNAS (USA) Nol. 94:10018–10023, Sep. 1997.

Strugnell et al. DNA vaccines for bacterial infections. Immunol. and Cell Biol. vol. 75:364–369, Apr. 1997.

Talwar Vaccines for control of fertility and hormone–dependent cancers. Immunol. Cell Biol. vol. 75:185–189, Feb.1997.

Willadsen Novel vaccines for ectoparasites. Vet. Parasitol. vol. 71:209–222, Feb. 1997.

Mons The problem of multiplicity in malaria vaccine development. Ann. Tropical Med. Parasitol. vol. 91: (supp. 1)S55–S58 Apr. 1997.

Sprent et al. Lymphocyte life–span and memory. Science vol. 265:1395–1399, Sep. 2, 1994.

Oldstone How viruses escape form cytotoxic T lymphocytes: Molecular parameters and players. Virol. vol. 234:179–185, Aug. 1997.

Rabinovich et al. Vaccine technologies: View to the future. Science vol. 265:1401–1404, Sep. 2, 1994.

Cohen Bumps on the vaccine raod. Science vol. 265:1371–1373, Sep. 2, 1994.

HLA-DR

α6β1 integrin

SPERM AS IMMUNOGEN CARRIERS

CROSS-REFERENCE TO RELATED APPLICATIONS

This application is a continuation-in-part of U.S. Ser. No.08/406,299, filed Mar. 17,1995, now abandoned, which is a continuation-in-part of U.S. Ser. No.08/343,008, filed Nov. 21, 1994 (now abandoned).

FIELD OF THE INVENTION

The present invention relates to vaccines, contraceptives and gene therapy strategies in which sperm cells or components thereof are used to deliver immunogens or nucleic acids to target cells. The invention also relates to in vitro assays for identifying candidate vaccine antigens.

BACKGROUND OF THE INVENTION

Vaccines

Sexually transmitted diseases (STDs) are caused by a wide range of different microbial pathogens, but recent studies have shown that each of these agents interacts with the others in ways that mutually promote their transmission between sexual partners. This is particularly true of HIV, whose sexual transmission is significantly more likely between individuals having existing disease caused by any of several non-HIV pathogens, such as genital herpes, Chlamydia, or gonorrhea. The World Health Organization has therefore concluded that the ongoing worldwide research effort toward an AIDS prophylactic vaccine should include an intensified push toward development of vaccines against other sexually transmitted diseases. While HIV is currently the only essentially universally lethal STD pathogen known, other STD agents cause significant morbidity and adversely affect fertility and reproductive health in adults. In addition, non-HIV STD pathogens, cause significant mortality in children.

Bacterial STD pathogens, such as *Chlamydia trachomatis, Hemophilus ducreyi, Neisseria gonorrhoea,* and *Treponema pallidum* cause repeated infections, and it appears that prior infection does not induce broadly effective immunity. Many of the non-HIV viral STD pathogens present the additional problem of persistence, wherein infection, once established, is lifelong. Although some of agents can be inactivated or attenuated by neutralizing antibodies in the laboratory, at present there appears to be no natural immune state that can be induced by vaccination.

Similarly, there are no effective vaccines against HIV infection despite the many different approaches under investigation. Like other viral STD pathogens, such as the genital herpes viruses and papillomaviruses, HIV is a persistent virus whose immunogenic epitopes exhibit variability in nature. There appears to be no natural immune state directed against HIV that can be mimicked by vaccination.

Vaccine development efforts have been further hampered by the discovery that systemic immunity induced by conventional vaccination in the available primate models does not protect against venereal infection. An example of this effect is seen in the chimpanzee model, in which HIV causes infection, but does not cause fatal disease. For a short time after vaccination, animals that have been vaccinated with recombinant HIV envelope glycoproteins produce serum antibodies that protect against viral challenges delivered intravenously. This short-term immunity, however, does not protect against viral challenge by mucosal routes.

In rhesus macaques, infection by the HIV-related SIV virus causes disease that is similar to human AIDS, but SIV viral or subunit vaccines administered intramuscularly do not induce protective immunity. More recent work with this model shows that systemic immunity against SIV can be induced by vaccination protocols in which intramuscular priming is followed by mucosal boosting with microencapsulated SIV or its components. Vaccination protocols that use low doses of live SIV delivered exclusively by intravaginal or intrarectal routes have also been shown to result in immunity against vaginal challenge with SIV.

After sexual contact, sperm elicit a transient leukocytic infiltration of the mammalian cervix (Thompson et al., *Am. J. Reprod. Immunol.,* 28:85, 1992), and human cervical cells are bound and penetrated by sperm at this time (Sievers-Altermann et al., *S. Afr. Med. J.,* 77:319, 1990). The primate SIV mac virus, a lentivirus closely related to HIV, causes an AIDS-like immunodeficiency disease in rhesus macaques (simian AIDS or SAIDS; Gardner, *Vaccine,* 9:787, 1991). Studies of SlVmac251 infection in cervicovaginal tissues of rhesus macaques have employed purified virus strains or their molecular clones for intravaginal infection or vaccination (Spira et al., *J. Exp. Med.,* 183:215, 1996). Studies of SAIDS in these animals have defined critical steps in transmission and early SIV pathogenesis that could not be studied retrospectively in HIV-infected or HIV-exposed humans (Spira et al., supra.). This animal model has also provided an excellent system for investigation of vaccine approaches to protection against HIV transmission from semen (Miller et al., *J. Virol.,* 68:6391, 1994; Miller et al., *J. virol.,* 71:1911, 1997; Gallichan et al., *J. Exp. Med.,* 184:1879, 1996).

Miller et al. have identified limiting doses of SlVmac251 or of the HIV/SIV recombinant strain SHIV89.6 that elicit a transient viremia without seroconversion in 33% of animals exposed by intravaginal injection. Animals that do not seroconvert are immune to challenge doses of pathogenic virus given by the same route. This result is not obtained after systemic vaccination with live virus, or with inactivated virus or with viral subunits delivered intravaginally. These data clearly demonstrate that vaccine protection against venereal SIV transmission is possible, but this protocol has limited prophylactic applicability because live virus can infect.

The foregoing illustrates that some success has been achieved through genital-mucosal administration of vaccines. Nevertheless, antigens in the mucosal microenvironment are degraded by mucosal cells, and vaccine formulations are poorly absorbed in the mucosa. Thus, antigen uptake, immunogenicity and stability of vaccines can all be problematic using this vaccination route.

CONTRACEPTIVES

A current area of contraceptive research is directed towards delivery of immunogens designed to prevent pregnancy. Existing contraceptive vaccines, however, are administered by conventional intramuscular injection and have a number of problems associated therewith. These problems include autoimmune responses, unpredictability of long-term or permanent immunity, and difficulty reversing immunity if pregnancy is later desired.

Gene Therapy

Gene therapy involves administering DNA to cells to permanently alter their protein expression phenotype and that of their progeny. Recent advances in gene therapy indicate that it may become a viable treatment option for cancer and a number of genetic diseases, and that vaccination with DNA might prove useful for immunization. Studies with DNA carried by sperm now suggest that gene therapy with ova and embryos may also allow for correction of genetic defects in germ line cells via fertilization. As with the vaccines and contraceptives discussed above, many problems associated with gene therapy relate to the delivery vectors.

SUMMARY OF THE INVENTION

There is provided in accordance with one aspect of the present invention a composition comprising a sperm cell carrier and an immunogen exogenous to the carrier, the immunogen being in a form suitable for coadministration with the carrier. The composition may be in a form suitable for delivery to rectal or vaginal tissue. The immunogen can be displayed on the surface of the carrier, incorporated into the nucleus of the carrier, or administered alongside the carrier, in which case the carrier serves as a natural adjuvant for the immunogen by crosslinking HLA-DR molecules simultaneously with immunogen-mediated stimulation of antigen-presenting cells, T cells or B cells. Particulate and soluble immunogens can be used. Examples of particulate immunogens include live attenuated bacteria, live attenuated viruses, inactivated bacteria, inactivated viruses, micelles, immune stimulating complexes (ISCOMS), liposomes, microspheres and lipid vesicles. Examples of soluble immunogens include proteins, peptides, nucleic acids, lipids and carbohydrates. Preferably, the vaccine also includes an adjuvant agent, such as BCG, *Brucella abortus* or Cholera toxin B, either attached to the sperm or administered alongside the sperm carrier complex as part of the vaccine formulation. Advantageously, the immunogen is derived from an STD microbial pathogen. Preferably, the pathogen is *Chlamydia trachomatis, Hemophilus ducreyi, Neisseria gonorrhea* or *Treponema pallidum.* In another aspect of this preferred embodiment, the immunogen is coupled to the carrier. Advantageously, the composition is in a form suitable for positioning of vaccine immunogens onto mucosal lymphoid cells for binding or uptake by the cells simultaneously with or prior to the interaction of the cells with sperm after sexual contact.

The present invention also provides an in vitro method for identifying a vaccine immunogen, comprising the steps of isolating peripheral blood mononuclear cells (PBMCs) from an individual, contacting the PBMCs with an antigen in the presence of a sperm cell carrier; and assaying proliferation of the PBMCs and production of cytokines, where enhanced proliferation of the PBMCs and cytokine production by the stimulated cells indicates that the antigen is a candidate vaccine immunogen, and identifies the arm of the immune response (cellular or humoral) stimulated by the vaccine immunogen carried by or accompanied by sperm. Preferably, the assaying step comprises incorporation of tritiated thymidine and identification of cytokines using methods known to those skilled in the art. In one aspect of this preferred embodiment, the antigen is coupled to the carrier. Advantageously, the antigen is derived from an STD microbial pathogen. The method may additionally comprise contacting the PBMCs with the antigen in the absence of the sperm cell carrier and comparing the proliferation of the PBMCs in the presence and absence of the carrier, wherein enhanced PBMC proliferation in the presence of the carrier indicates that the antigen is a candidate vaccine immunogen.

DETAILED DESCRIPTION OF THE INVENTION

The present invention relates to vaccines, contraceptives and gene therapy strategies in which sperm cells or components thereof are used to deliver immunogens and nucleic acids to target cells.

I have discovered that human sperm bind and enter somatic cells through interactions involving the cell surface histocompatibility molecule HLA-DR. HLA-DR expression is usually limited to cells originating in the bone marrow, such as antigen-presenting mucosal cells. Thus, the specificity of sperm for this marker allows for targeted presentation of small amounts of sperm-bound immunogen to antigen-presenting cell populations present in mucosal tissues.

Sperm/HLA-DR binding mimics one of the two ligand binding activities of superantigens (sAg) (Kotzin et al., Adv. Immunol., 54:99, 1993). In cultured primary leukocytes or cell lines, ligation of class 11 MHC molecules by antibody or with sAg triggers homotypic binding reactions, promotes antigen presenting cell (APC) interaction with T cells and amplifies target cell activation responses to a variety of stimuli, including HIV, polyclonal mitogens and recall antigens (Odum et al., *Eur. J. Immunol.,* 21:2121, 1991; Tumang et al., *J. Exp. Med.,* 171:2153, 1990; Fuliehan et al., *J. Immunol.,* 146:1661, 1991). Like sAg, sperm trigger homotypic binding, increase HIV infectivity, and amplify leukocyte responses to mitogens or specific antigens (Kotzin et al., supra.).

I have also discovered that HIV binds selectively to capacitated sperm from normal semen, that viral antigens are present on the surface of and inside such sperm, and that HIV DNA is associated with sperm from HIV-infected men. During sexual contact, such sperm may selectively bind to target cells in mucosal tissues and T cell markers, such as CD4, and the sperm bind to HLA-DR. In this way, HIV-bearing sperm resemble bacterial superantigens, which simultaneously engage MHC class II molecules and the V-beta domain of the T cell antigen receptor on T cells. Thus, I believe that sperm/HLA-DR binding can confer superantigen status to other immunogens carried on sperm membranes.

I believe that the specificity of sperm for HLA-DR can also amplify HIV infectivity by stimulation of the immune system. In addition to its known role in presenting antigen to T cells and regulating T cell growth, HLA-DR is a signal transducing receptor whose ligation activates cells and is central to immune responses. The binding specificity of sperm mimics that of bacterial superantigens, which trigger target cell activation through direct binding to HLA-DR and to T cell receptors of identified V-beta families. Since activated cells are much more susceptible to HIV infection, these interactions promote infection of the target cells by any HIV present in the semen.

Thus, the ability of sperm to bind to HLA-DR results both in targeting to antigen-presenting mucosal cells, and in activation of the immune system via activation of the same target cells. This targeting/activation mechanism can be exploited as a strategy for targeting vaccine immunogens or nucleic acids to cells in mucosal tissues that express HLA-DR, for their delivery to HLA-DR expressing target cells in vitro, or for their delivery to ova in vitro or in vivo. For example, sperm carrying HIV or subunits thereof can be used to selectively bind and stimulate T cells in mucosal tissues that express HLA-DR, CD4 and/or T cell receptors of certain V-beta families.

The specific mode of sperm interaction with such cells could be further altered by adding additional ligands to the sperm membrane. Examples would include class I or class II molecules, or peptides thereof, which have been selected or generated to ensure allogenicity with respect to the recipient. Alternatively, sperm vaccines could carry identified superantigenic microbes, such as *Brucella abortus,* or superantigenic components of such agents, such as Staph exotoxin, to ensure engagement of particular subsets of T cells or particular subsets of T cells expressing identified V-beta T cell receptor families. Other additional components could include specific binding ligands conferring or amplifying binding to certain HLA-DR expressing cell types. An example of such a ligand would be ICAM-1, which engages C3 receptors on macrophages.

In the sexual contact microenvironment, prophylactic vaccination against certain sexually transmitted disease pathogens can require a weighted triggering of cellular immunity relative to humoral immunity. For HIV, for example, cellular immune responses kill infected cells and virus as well, but antibodies prevent effective vaccination, both by masking immunizing epitopes and promoting target cell infection via Fc receptors for bound antibody. Sperm engagement of HLA-DR on target cells also triggers signal-ling via IL-2 receptors, thereby engaging T cell populations that trigger cellular immune responses. Sperm entry into target cells via HLA-DR is followed by sperm fusion or endo/phagocytosis and entry into the target cells. Immunogens carried by the sperm are therefore exposed to HLA Class I antigen processing pathways that selectively trigger cellular immune responses.

In addition to their cellular targeting and antigen presentation capabilities, sperm are an effective packaging vector which protect immunogens, adjuvants, nucleic acid and other components incorporated therein from mucosal cell degradation. In particular, immunogens carried by m are incorporated into the sperm membrane or nucleus, where they remain until the sperm are degraded inside phagocytic or antigen-presenting cells.

Furthermore, HIV virions incorporated into sperm become naturally replication-defective because sperm DNA does not allow integration of provirus. In addition, under certain circumstances HIV binds and fuses with sperm membranes, but the viral nucleocapsids do not disassemble due to oxidant damage to the viral core protein. After such interactions, HIV may be rendered noninfectious, while conserving its full antigenic profile and acquiring mitogenic capabilities for target cells via its association with sperm.

Sperm cells or components thereof can be used with all immunogens currently being tested in candidate vaccines against HIV, including viral subunits such as viral envelope proteins, $V_3$ loop peptides, and peptides from other viral proteins. Other immunogens that can be used for HIV vaccination using the sperm vaccination protocol, include live or inactivated whole virus, live or inactivated attenuated virus, live or inactivated recombinant virus, viral subunits encoded by recombinant viral or bacterial agents, pseudovirus, other viral vectors, bacterial vectors, and naked DNA.

Sperm can also be exploited for development of vaccines against sexually transmitted disease pathogens other than HIV. In this context, a number of different immunogens can be used, including attenuated bacteria, attenuated viruses, microbial subunit proteins and peptides thereof.

In each case, amplification of immunogen efficacy and directed stimulation of selected components of the host immune system can be further accomplished by a variety of methods well known to those of skill in the art, including the use of microbial or chemical adjuvant agents, selected mitogens such as dextran sulfate, other microbial agents or subunits thereof, including DNA encoding such subunits, or nucleic acids encoding cytokines, all of which can be introduced with the vaccine or incorporated into the sperm vector itself. In addition, components conferring additional targeting or adjuvant capability can be added to the sperm carrier or to vaccine formulation, whether or n the carrier is associated with the primary immunogen component of the vaccine.

Vaccine and contraceptive immunogens can be delivered in a number of ways, including (a) as added components of live, inactivated sperm cells; (b) as components of microvesicles, liposomes, micelles, or microbes (such as BCG or *Brucella abortus*) carrying sperm membrane carbohydrates, lipids, and/or proteins; (c) as components of microvesicles, liposomes, micelles, or microbes containing the isolated HLA-DR binding molecule(s) from sperm; (d) as part of a molecular complex containing sperm membrane carbohydrates, lipids, and/or proteins, or containing the isolated HLA-DR binding molecule; or (e) as agents delivered together with live, inactivated sperm, artificial vesicles containing cell-binding sperm molecules, or soluble preparations containing such molecules.

The sperm cell carrier-immunogen compositions of the invention can also be used in vitro to identify vaccine immunogen candidates which are subsequently tested in vivo. Sperm are combined with any desired immunogen, preferably one derived from an STD pathogen, and added to peripheral blood mononuclear cells (PBMCs) obtained from an individual. The antigen can either be coupled to the sperm or administered alongside sperm as described herein. Proliferation of PBMCs is then assayed by the well known $^3$H-thymidine incorporation assay in which PBMCs are pulsed with $^3$H-thymidine 2–3 days after antigen or antigen/sperm administration (Via et al, *J. Immunol.*, 151:3914, 1993; Shearer et al., *Trends Biotechnol.*, 15:106, 1997), both of which are hereby incorporated by reference. In this assay, T-cells are stimulated indirectly via macrophages. The label is taken up into dividing cells and incorporated into DNA. Sperm cell-immunogen compositions which significantly enhance cell proliferation compared to control compositions lacking sperm are thereby identified as vaccine candidates for the particular immunogen.

Figure 1A:
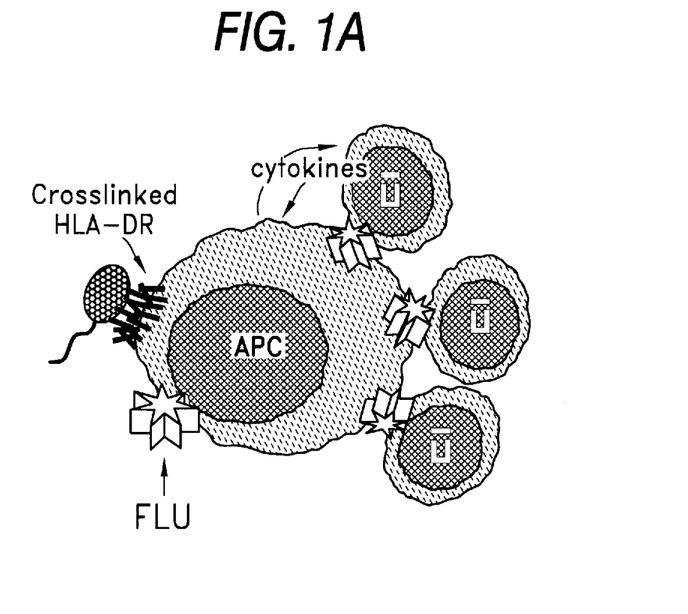
FIG. 1A is a schematic diagram showing sperm augmentation of APC presentation of influenza virus A, or FLU, and promoting necessary adhesion receptor interactions which amplifies T cell recruitment by APC and T cell activation by processed FLU antigen.
Figure 1B:
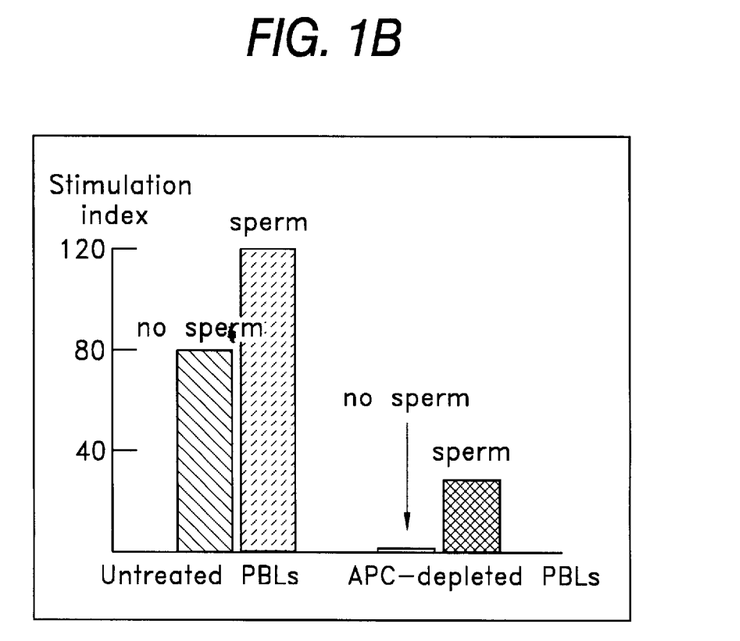
FIG. 1B shows a PBMC proliferation assay in which FLU was added to isolated peripheral blood mononuclear cells (PBMCs, either untreated or APC-depleted) in the presence or absence of sperm.

When sperm were added to PBMC together with a recall antigen (influenza virus A, or FLU; FIG. 1A), cell proliferation in relation to antigen4ree cultures was significantly increased (50% increase), particularly if the APCs in the cultures were depleted prior to co-culturing (400% increase) (FIG. 1B). The cell proliferation assay was perform by incorporation of tritiated thymide, as described. Sperm may replace APC by functional augmentation of APC remaining in APC-depleted cultures, co-activation of B cells recognizing FLU antigen, or both.

Figure 2A:
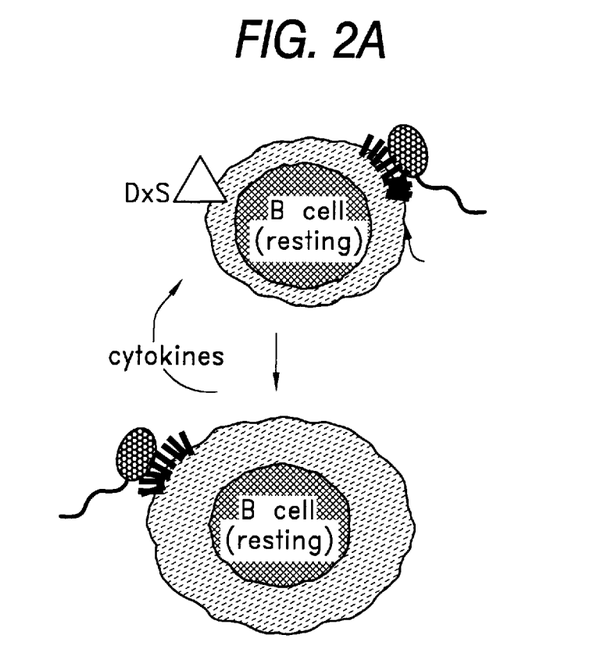
FIG. 2A is a schematic diagram showing that sperm ligation of B cell HLA-DR amplifies signaling by the B cell mitogen dextran sulfate (DxS) via HLA-DR crosslinking and cytokine production.
Figure 2B:
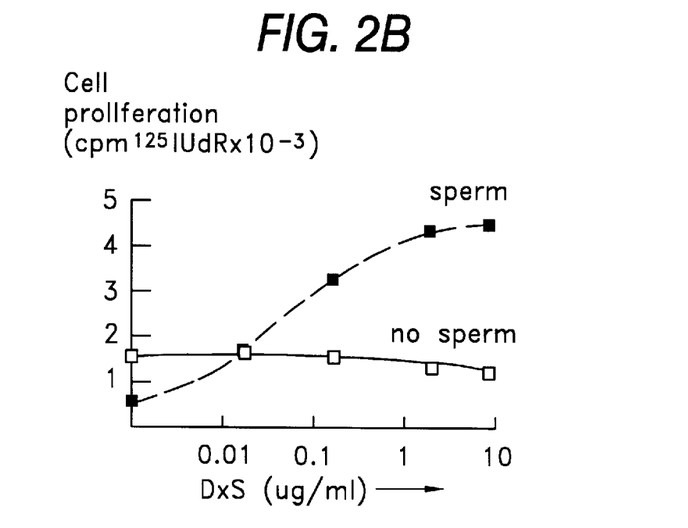
FIG. 2B is a graph showing the results of a B cell proliferation assay using DxS either in the presence or absence of sperm. Cell proliferation was assayed by incorporation of $^{125}$I-UdR.

Cell aggregation and target cell activation by sperm also augmented PBMC activation by B cell mitogen (FIG. 2A). In PBMC cultured with the B cell mitogen dextran sulfate (DxS), sperm enabled cell proliferation in response to mitogen doses that were ineffective without sperm (FIG. 2B).

Preparation Of Vaccine In Which Immunogens Are Carried By Sperm Cells

In accordance with a first aspect of the present invention, immunogens are delivered as added components of intact, normal sperm cells.

In accordance with this aspect of the present invention, sperm donors are selected by screening healthy males for infection by blood-borne and sexually transmitted pathogens, using tests and technologies well known to those of skill in the art. Semen from donors screening clear of infection is collected in sterile tissue culture tubes and allowed to liquify for approximately 10 minutes. The semen is then layered onto a discontinuous gradient of Percoll (Pharmacia) diluted in a medium, such as Ham's F-10. After centrifugation, the pellet fraction containing the sperm is collected and washed by repeat centrifugations in medium, such as Ham's F-10.

Capacitation is induced in the isolated sperm to expose the HLA-DR binding sites. Capacitation can be accomplished using a number of methods well known to those of skill in the art. For example, capacitation can be induced by incubating the isolated sperm for approximately 2–12 hours in a salt solution containing an energy source and protein, such as Tyrode's solution with 0.5% human serum albumin.

After capacitation, the sperm are incubated with microbial or molecular immunogens in order to couple the immunogens to the sperm cell carrier. If particulate immunogens, such as bacteria, viruses, micelles, liposomes, microspheres or lipid vesicles are used, capacitated sperm and a suspension of the particulate immunogen suspension are incubated together. Preferably incubation is at 37° C. for approximately 10 minutes to 16 hours, and more preferably for 1–3 hours.

If soluble immunogens, such as proteins, peptides, or nucleic acids, are used, the capacitated sperm and immunogen solution are incubated for varying periods of time, depending upon the sperm interaction characteristics of the individual macromolecules. Preferable incubation times at 37° C. are approximately 10 minutes to 16 hours, and more preferably, from 1–3 hours.

Typically, incubation of immunogen with the sperm carrier results in sufficient coupling of the immunogen to the sperm to provide an immunologically effective dose of immunogen. However, in the absence of sufficient natural binding, coupling/cross-linking agents can be used to aid in coupling the immunogen to the carrier. A typical agent now in common use is sulfo-SMCC, which covalently links amino groups to sulfhydryl groups on proteins. For cells or macromolecules lacking surface sulfhydryl groups, these can be added with 2-ininothiolane prior to the ligand coupling step.

Adjuvant can be incorporated into the vaccine to further selectively activate cellular immunity. The adjuvant agent can be incorporated into the surface of the carrier or administered alongside it. Exemplary adjuvant agents include microbial immunogens such as BCG, *Brucella abortus*, or active components thereof. For HIV vaccination, *Brucella abortus* or its isolated lipopolysaccharide is preferably used. Alternatively, the sperm themselves may serve as adjuvants by crosslinking HLA-DR in the presence of the immunogen.

After incubation, the sperm/immunogen suspension is washed by repeated centrifugation in Ham's F-10 medium. After washing, the sperm should be inactivated to prevent pregnancy. Inactivation can be by any of a number of methods well known to those of skill in the art, such as irradiation, which damages the sperm DNA; sonication, which removes the sperm tail; or snap-freezing, which causes tail damage secondary to lipid peroxidation. Sperm inactivation caused by lipid peroxidation can also be achieved by treatment with a lipid peroxidation promoter system, such as ascorbic acid and ferrous sulfate. In addition, sperm inactivation can be accomplished by fixation using substances such as formaldehyde, paraformaldehyde, and glutaraldehyde. In some instances it is desirable to inactivate the sperm prior to coupling with the immunogen.

The sperm-carried immunogen is combined with inert ingredients well known to those of skill in the art to produce a physiologically administrable form of the vaccine. A variety of different physiologically administrable forms can be used, such as douche, diaphragm, implant, suppository, lozenge, intramucosal gun injection, intravenous injection, subcutaneous injection or intramuscular injection. However, mucosal delivery is a preferred form of delivery of the present invention.

Preparation Of Vaccine In Which Immunogens Are Delivered By A Carrier In Which A Sperm Membrane Lysate Is Incorporated Immunogen targeting capability can also be achieved in accordance with a second aspect of the present invention using a sperm membrane lysate in which HLA-DR binding activity has been preserved.

In accordance with this aspect of the present invention, sperm are isolated from the semen of healthy donors and washed as previously described in accordance with the first aspect of the present invention. Sperm membrane carbohydrates, lipids and protein are extracted using methods well known to those of skill in the art. Preferably, nonionic detergents, such as Triton X-100 or CHAPS, are used in the extraction step.

The extracted molecules of the sperm membrane lysate are then assembled into or adsorbed onto any of a variety of carriers, including liposomes, immunogen stimulating complexes (ISCOMS), micelles, microvesicles, or microbes, such as BCG or *Brucella abortus*. Incorporation into liposomes can be accomplished using a variety of methods well known to those skilled in the art. For instance, lipid drydown methods can be used followed by resuspension in aqueous solutions containing saponins, such as Quil A. Alternatively, extracted proteins can be coupled to proteins containing a glycosylphosphatidylinositol (GPI) signal, such as the decay accelerating factor of complement, which allows incorporation into GPI iposomes.

After the extracted sperm membrane molecules have been incorporated into a carrier, the carrier is incubated with microbial or molecular immunogens in order to couple the immunogens to the carrier as viously discussed above. Coupling/cross-linking agents and/or adjuvant agents can also be used, as also previously discussed.

After incubation, the coupled immunogen/carrier is washed and inert ingredients are added to produce a physiologically administrable vaccine as discussed above in accordance with the first aspect of the present invention.

Preparation Of Vaccine In Which Immunogens And An HLA-DR Binding Molecule Are Coupled In A Molecular Complex In accordance with a third aspect of the present invention, immunogen targeting capability can be achieved using a molecular complex in which an immunogen is coupled to an HLA-DR binding molecule. In accordance with a preferred embodiment of this aspect of the present invention, the HLA-DR binding molecule is isolated from sperm. The HLA-DR binding molecule can be any molecule which binds HLA-DR, including a protein, a lipid or a carbohydrate.

Determination Of Sperm PH-30 Binding To HLA-DR

Figure 3:
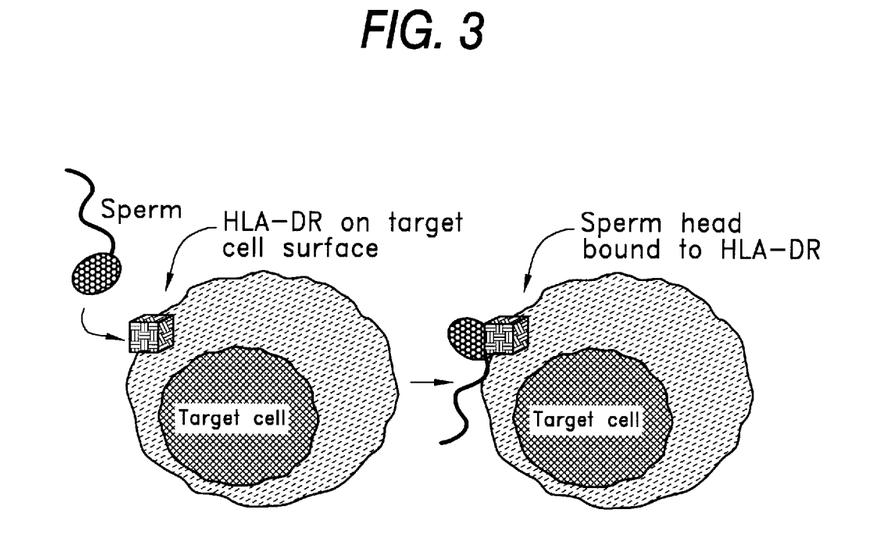
FIG. 3 is a schematic diagram showing binding of sperm to HLA-DR on the target cell surface.
Figure 4A:
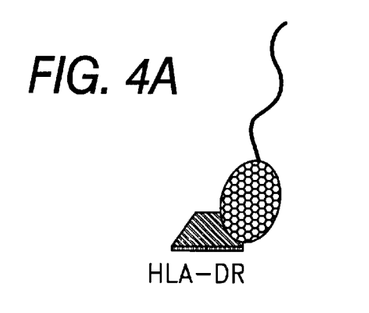
FIG. 4 is a schematic diagram showing human sperm binding to somatic cell HLA-DR (a), binding of mouse sperm PH-30 to somatic cell VLA integrin (b) and association of HLA-DR and VLA association via tetraspans molecules (c).
Figure 4B:
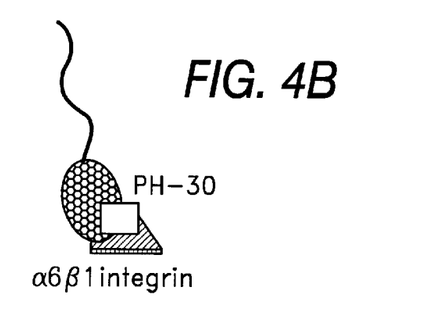
Figure 4C:
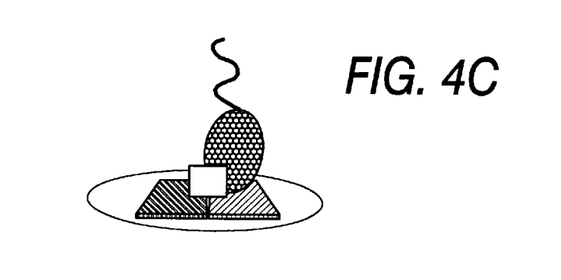

To understand sperm-target cell interactions involving HLA-DR, it is important to identify all of the sperm molecules and target structures involved. While human sperm bind HLA-DR on somatic cells (FIG. 3; Ashida et al., *Proc. Natl. Acad. Sci. U.S.A.*, 84:3395, 1987; Scofield et al., *J. Immunol.*, 248:1718, 1992), mouse sperm bind to the $\alpha_6\beta_1$ integrin on eggs and on somatic cells via the sperm PH-30 and other disintegrin molecules (FIG. 4; Almeida et al., *Cell*, 81:1096, 1995). The PH-30 disintegrin is a heterodimer whose beta chain contains an integrin ligand-binding domain (Blobel et al., *Nature*, 356:248, 1992). Although this would seem to suggest that mouse and human sperm binding to somatic cells are governed by different receptor binding events, primary binding in both cases may be to VLA integrins (FIG. 4). On cells that express both molecules, HLA-DR and VLA integrins are members of tightly associated molecular complexes that also contain several transmembrane-4 (tetraspans) family molecules (FIG. 4; Rubinstein et al., *Eur. J. Immunol.*, 26:2657, 1996). The following experiments compare human and mouse sperm-somatic cell binding events to define the role played by integrins and tetraspans molecules in each case.

To determine whether human sperm PH-30 participates in HLA-DR binding, anti-PH-30, anti-VLA integrin and anti-CD9 (tetraspans) antibodies are tested for inhibition of sperm binding to mouse 3T3 or L cells expressing transfected human HLA-DR or VLAβ1 integrins(Scofield et al., *J. Immunol.*, 248:1718,1992;Almeida et al., supra.; Rubinstein et al., supra.). To determine whether mouse sperm bind to murine I-E, the murine counterpart of human HLA-DR, and VLA integrin together, mouse 3T3 cells are transfected with the α and β chains of I-E. These transfected cells are used to determine whether mouse sperm bind to these cells and not to their nontransfected counterparts, and, if so, if binding is inhibited by anti-PH-30, anti-l-E, and anti $\alpha_6$ or $\beta_1$ integrin antibodies.

To identify and isolate HLA-DR binding proteins from sperm or other sources, soluble HLA-DR can be coupled to a solid support, such as Sepharose beads (Pharmacia), to construct affinity columns. Detergent lysates of sperm membranes are produced, as discussed above. The lysates are passed over the columns so that HLA-DR binding protein contained in the lysate is retained on the column. Retained HLA-DR binding protein can then be eluted.

HLA-DR binding proteins eluted from the solid support can be characterized by polyacrylamide gel electrophoresis to assess molecular weight and subunit structure. The protein subunits can then be separated by two-dimensional ("2D") gel electrophoresis. The 2D gels can then be blotted and probed with antibody against known molecules suspected to be related or identical to the HLA-DR binding protein. The blotted proteins can also be digested for N-terminal microsequencing. The amino acid sequence information can be used to search existing databases for related gene sequences in order to identify the eluted protein or to identify additional, related proteins that might have HLA-DR binding capabilities.

If the N-terminal sequence information is insufficient for conclusive identification of the eluted protein, the N-terminal sequence data can be used to construct oligonucleotide primers for PCR amplification of encoding gene sequences. Oligonucleotide probes can then be constructed to identify encoding genes. Identified genes can be cloned into appropriate expression vectors to produce glycated HLA-DR binding protein. Structure-function studies can then be conducted to confirm that the synthesized protein retains the HLA-DR binding characteristics of the native structure present in the sperm membrane.

As discussed above, the sperm membrane HLA-DR binding ligand may also be a lipid or a carbohydrate. Neutral lipids, phospholipids and glycolipids, whose binding characteristics may be governed by their lipid moieties and/or carbohydrate moieties, can be isolated from detergent-solubilized sperm membrane preparations by aqueous two-phase polymer methods. Alternatively, isolation can be accomplished by thin layer chromatography (TLC) using organic solvents.

For characterization of isolated lipids, TLC employing known lipid standards can be used. HLA-DR binding characteristics are tested by overlaying the TLC plates with membrane lysates or soluble ligands, such as soluble HLA-DR, followed by incubation with radio labeled anti-HLA-DR antibody and autoradiography.

Characterization of isolated carbohydrates having the ability to bind HLA-DR can be accomplished by well known techniques using specific glycosidases.

After the HLA-DR binding molecule has been isolated, it is incubated with microbial or molecular immunogens in order to couple the immunogens to the HLA-DR binding molecule as previously discussed in accordance with the first aspect of the present invention. Coupling/cross-linking agents and/or adjuvant agents can also be used, as previously discussed.

After incubation, macromolecular complexes containing both components can be isolated, such as by gel filtration. The complexes are washed and inert ingredients added to produce a physiologically administrable vaccine, as discussed above in accordance with the first aspect of the present invention.

Alternatively, after isolation, mixed or isolated lipids from these extracts can be rehydrated to form liposomes for subsequent adsorption to carriers such as BCG, or they can be mixed with immunogen formulations to make liposome-enclosed vaccines, as discussed previously in accordance with the second aspect of the present invention.

Effects Of Sperm On Antigen Recognition

Figure 5A:
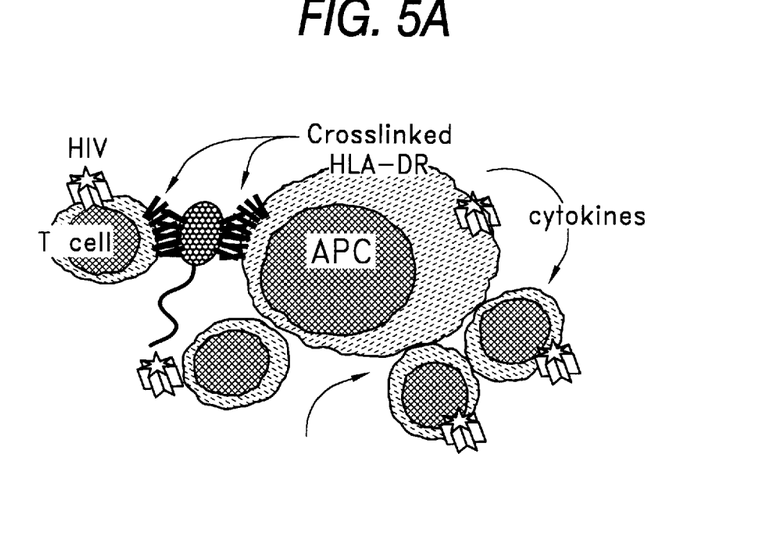
FIG. 5A is a schematic diagram showing that sperm ligation of HLA-DR activates antigen presenting cells (APC) and T cells, increasing HIV entry and replication in both cell types. Activated APC and T cells aggregate via new adhesion molecules, increasing HIV replication, accelerating cell-to-cell transfer of virus and promoting syncytium formation.
Figure 5B:
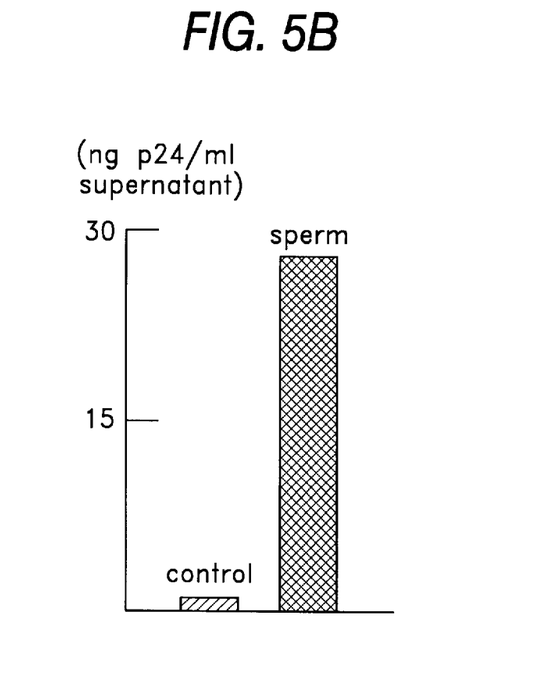
FIG. 5B is a graph showing HIV replication in PBMC in the absence and presence of sperm as measured by a conventional p24 assay.

In cultures of activated PBMCs, HIV and sperm together promoted rapid cell aggregation (within 2 hours postinfection) around giant cells filled with sperm (FIG. 5A). After 2 weeks, such cultures produced 10–100 times more progeny virus as determined by p24 assay than did control cultures infected without motile sperm (FIG. 5B). HIV infectivity enhancement by sperm may result from target cell aggregation, direct target cell activation, cytokine production or a combination of these effects.

The following experiments test the ability of sperm to prime T cell responses to recall antigen in PBMC cultures, using well characterized experimental systems designed for identification and testing of immunopotentiating agents in vitro. To assess sperm effects on antigen recognition, a functional analysis of T cell responses to FLU and other recall antigens is conducted in human PBMC cultures, with or without sperm, using cell proliferation and cytokine production as indices of response (Via et al., supra.; Shearer et al., supra.). MHC self-restricted and unrestricted antigen (FLU vs. allogeneic cells) are used to determine whether sperm affects these recognition events differentially. Sperm effects on monocytes, B cells or T cells are also tested by limiting dilution add-back of sperm-stimulated cells to PBMC cultures. APC-depleted PBMCs and Transwell cultures are used to assess the relative importance of cell contact and cytokines in these interactions. Index cytokines denoting Th1- vs. Th2-responses (leading to cellular vs. humoral immunity; Shearer et al., supra.) are identified in PBMC supernatants, monocyte supernatants, T and B cells stimulated in isolation and in combination with each other and with PBMCs (add-back experiments).

Use Of Sperm As Adjuvants In SIV Vaccines

Figure 6A:
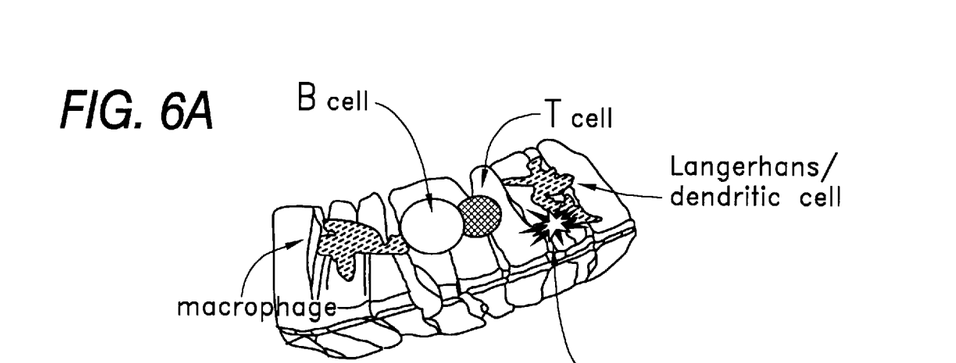
FIGS. 6a and 6b are diagrammatic cross-sections of primate genital-mucosal epithelium that identify lymphoid cell types relevant to SIV infection and immunity, including Langerhans/dendritic cells, which have been identified as primary targets for free SIV injected intravaginally, and showing how inactivated SIV or SIV subunits may interact with such cells, either alone (a) or in the presence of sperm (b).
Figure 6B:
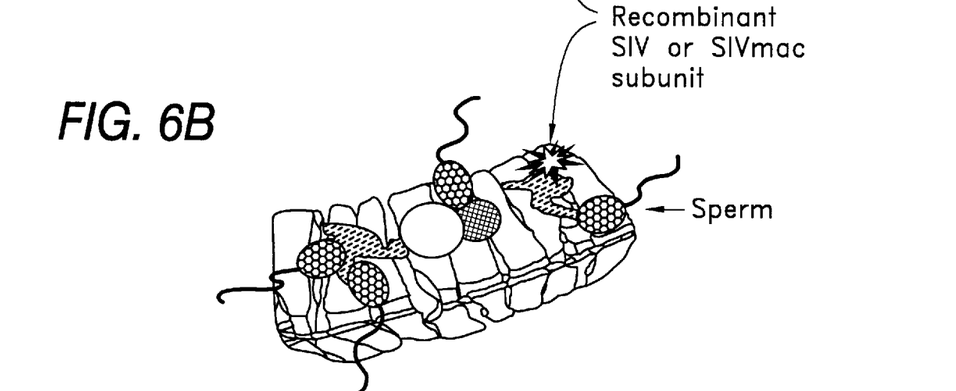

The conditions required for vaccine protection against genitally transmitted viral or bacterial STD pathogens generally reflect those occurring in natural infection, wherein live agents delivers themselves efficiently into cervicovaginal target cells for recognition by T cells (Gardner, supra.). FIG. 6 shows diagrammatic cross-sections of primate genital-mucosal epithelium (vagina, cervix, rectum, urethra) that identify lymphoid cell types relevant to SIV infection and immunity (including the Langerhans/dendritic cells which are APCs and potential primary targets for SIV infection; Spira et al., supra.; Lehner et al., Adv. Exp. Med. Biol., 371A:357,1995). This figure also shows how inactivated SIV or SIV subunits might interact with such cells, either alone (a) or in the presence of sperm (b).

To test sperm as SIV vaccine adjuvants in rhesus macaques, 12 juvenile animals (male and female) are vaccinated intramuscularly with the recombinant HIV/SIV strain 89.6 (SHIV89.6; Miller et al., J. Virol., 71:1911, 1997), either alone as a negative control (4 animals), with alum as a positive control for adjuvant activity (4 animals), or with sperm as the test vaccine (4 animals). Animals receive secondary immunizations at one and two months post-injection. Blood and rectal/cervicovaginal secretions from immunized animals are tested biweekly for six months for antibody to SIV (Miller et al., J. Virol., 68:6391, 1994; Miller et al., J. Virol., 71:1911, 1997). Sperm show significant adjuvant activity as evidenced by increased titers of serum or mucosal antibody.

Twelve mature female rhesus macaques are intravaginally inoculated with SHIV89.6 alone (6 animals) or with SHIV89.6 with sperm (6 animals), and then challenged with a limiting dose of SlVmac239 (pathogenic strain; Miller et al., J. Virol., 71:1911, 1997) at six seeks post-immunization. After challenge virus inoculation, the animals are followed for six months for viremia and seroconversion, with testing of their blood and rectal/vaginal secretions for anti-SIV antibody. Vaccinated animals are resistant to pathogenic virus challenge. A third group of vaccinated animals are sacrificed at different times after vaccination and/or challenge to determine localization of sperm and virus in cervicovaginal lymphoid tissues, for detection of activation markers and cell adhesion molecules on the lymphoid cells, and for in vitro functional analysis of cytotoxic T lymphocytes isolated from these locations.

Preparation Of Contraceptives In Which Immunogen Are Carried By Sperm Cells Delivered By Carriers Incorporating Sperm Lysates, Or Coupled In A Molecular Complex With HLA-DR Binding Molecules From Sperm, or Delivered Alongside Sperm By allowing targeted and amplified delivery of immunogens designed to prevent pregnancy, or by serving as natural adjuvants for such immunogens, the sperm vaccination protocol of the present invention can also be exploited for development of contraceptive vaccines in accordance with a fourth aspect of the present invention.

In accordance with this aspect of the present invention, sperm are isolated from the semen of healthy donors, washed, and either capacitated, as previously described, or subjected to membrane lysis or fractionation/isolation procedures, as also described above. The capacitated sperm cells, membrane lysate/carrier complexes or molecular complexes are then incubated with immunogen in order to couple the immunogen thereto as described above in accordance with the first, second and third aspects of the present invention.

A variety of immunogens can be used in accordance with this aspect of the present invention, such as those which elicit antibodies against molecules necessary for fertilization, maintenance of pregnancy, or spermatogenesis. Exemplary immunogens include whole human chorionic gonadotropin (hCG), its beta subunit, and the C-terminal peptide 109–145 thereof, which may be presented in variable sequence manifestations to "promiscuous" T cell epitopes thereby enabling effective immunization regardless of HLA haplotype. The foregoing hCG-related immunogens elicit antibodies against polypeptide hormones necessary for the maintenance of pregnancy. Other immunogens that can be used include the egg envelope protein ZP3, peptide/oligosaccharide subunits of ZP3, and sperm membrane proteins such as SP10, SP56, PH-20, PH-30 and lactate dehydrogenase (LDH), which elicit antibodies that prevent fertilization or that bind uniquely to sperm cells. SP10 and SP56 also elicit antibodies which bind to pre-implantation embryos and the egg envelope protein ZP3, respectively.

Because the HLA-DR binding protein isolated from sperm discussed above in accordance with the third aspect of the present invention may also be neces for fertilization, it may also be used to elicit antibodies that interfere with fertilization.

The sperm vaccination format can also be used to deliver gonadotropin releasing hormone (GnRH) or follicle stimulating hormone (FSH) as immunogens to trigger production of antibodies preventing sperm production by blocking hormonal maintenance of spermatogenesis. SP56, PH20 and LDH may also be delivered via the sperm vaccination format to trigger production and antibodies which interfere with sperm production and viability by active lysis of developing and mature sperm cells.

After incubation, the coupled immunogen/carrier is washed as discussed above in accordance with the first three aspects of the present invention. In those cases in which sperm is used as the carrier, the sperm is inactivated to prevent pregnancy as previously discussed in accordance with the first aspect of the present invention.

The coupled immunogen/carrier is combined with inert ingredients, as discussed above in accordance with the first aspect of the present invention, to produce a physiologically administrable form of the contraceptive. Alternatively, the vaccine immunogen may be administered in a formulation that positions the immunogen for interaction with and uptake by APC, T or B cells that interact with sperm after sexual contact.

Preparation of Sperm as Somatic Gene Therapy or DNA Vaccine Vectors

There are a number of problems associated with gene therapy. Most of the retroviral vectors now in use for gene therapy infect a broad range of cell types, which limits their potential efficacy for systemic administration. Attempts to deal with this problem have involved genetic engineering of the retroviral vectors to produce envelope proteins which incorporate specific ligands for identified receptors on the desired target cells. However, even if such approaches circumvent some of the existing problems in gene therapy technology, the requirement for complex genetic engineering for each use may limit the usefulness of these gene therapy approaches in human disease. The use of sperm as delivery vectors for exogenous DNA can remove the necessity for genetic engineering for delivery of DNA to somatic cells. In addition, such sperm have en shown to enable efficient delivery of exogenous gene sequences to ova.

In accordance with a fifth aspect of the present invention, sperm or sperm HLA-DR binding components are exploited as gene therapy vectors for delivery of genetic constructs to HLA-DR expressing somatic cells both in vitro and in vivo.

In accordance with this aspect of the present invention, DNA constructs containing therapeutic gene sequences, or sequences encoding immunogens, are incubated with sperm using well-established protocols for sperm incorporation of exogenous DNA. See Lavitrano, et al., *Molec. Reprod. Develop.*, 31:161 (1992) and Francolini, et al., *Molec. Reprod. Develop.*, 34:133 (1993), the disclosures of which are hereby incorporated by reference.

Selected gene sequences can be incubated with the sperm as components of microbial agents whose genomes contain the selected gene sequences, as components of engineered gene constructs containing such sequences (e.g., plasmids), or as components of whole DNA preparations isolated from cells containing such sequences.

Alternatively, genetically engineered microbial carriers carrying selected gene sequences, native microbes carrying adsorbed sequences, or microvessels containing such sequences could be used. Vaccine immunogens could also be combined with selected gene sequences to produce combined immunogen/DNA vaccines. Such approaches eliminate the complicated genetic engineering now required for use with existing retroviral delivery vectors, which must either carry the selected gene sequences within their genomes in orientations that do not interfere with viral entry and integration of the gene sequences, or which must be pseudotyped or contained within a different viral envelope to allow for binding and entry into selected cell types.

As with the HIV/STD/contraceptivevaccine strategy discussed above, carriers other than sperm cells can also be used, such as particulate carriers associated with a sperm membrane lysate containing HLA-DR binding components, or a molecular complex containing the HLA-DR binding molecule isolated from sperm. Additional ligands can also be incorporated into the sperm membrane, the sperm membrane lysate, or the sperm molecular complex to target genherapy constructs to selected cell types as discussed above in accordance with the first four aspects of the present invention.

Administration Protocols

Because all mucosal tissues contain large numbers of resident HLA-DR positive antigen presenting cells, the vaccines, contraceptives, and gene therapy constructs of the present invention are preferably delivered to mucosal tissue, such as the oral and intratracheal mucosae, the mucosal tissue of the female reproductive tract and the rectum of both sexes. Sperm vaccine formats of the present invention may also involve immunization by other routes, including subcutaneous, intramuscular, intravenous and intrathecal delivery.

Depending on the route of administration, administration of the vaccine contraceptive or gene therapy formulation can be accomplished using any of several physiologically administrable forms, including pill, capsule, lozenge, douche, diaphragm, implant, suppository, intramucosal gun injection, or conventional syringe.

Primary vaccination can be followed by booster immunization using the same physiologically administrable form or a different physiologically administrable form depending on the immunogen being delivered. The present invention overcomes the difficulties previously experienced with mucosal administration. Thus, for example, immunization against HIV can be solely by genital-mucosal administration, such as intravaginal or intrarectal administration. Combined routes of administration can also be used, such as primary immunization via intramuscular injection followed by intramuscular and/or mucosal boosting. The frequency and total number of booster immunizations can vary widely, depending on the formulation and route of administration. However, one of ordinary skill in the art can readily determine the appropriate immunization procedure using routine monitoring for the systemic or local presence of cytotoxic T lymphocytes specific for immunogenic epitopes or for the presence of secretory or serum antibodies which bind to epitopes on the vaccine immunogens.

Using ordinary skill in the art, such as by for weight, heart rate and other differences between humans and rhesus macaques as well as differences between the HIV and SIV viruses, typical immunization schedules for humans can be readily adapted from protocols found to protect rhesus macaques from subsequent challenge with SIV by mucosal routes. See Lohman, et al., *J. Med. Primatol.*, 28:95 (1994), Clerici, et al., *AIDS*, 8:1391 (1994), Miller, et al., *J. Virol.*, 68:6391 (1994), and Marx, et al., *Science*, 260:1322 (1993), the disclosures of which are hereby incorporated by reference.

Immunogen dosage can also vary, depending on the formulation and route of administration. Typical ranges for most immunogens are approximately 1–50,000 micrograms of immunogen per primary or booster immunization, more preferably 10–5,000 micrograms of immunogen per dose, and still more preferably 100–500 micrograms of immunogen per dose. Gene dosage for gene therapy would also vary depending on the construct being used.

For example, one HIV vaccination protocol in accordance with the present invention involves primary immunization via intramuscular injection of vaccine containing 100 micrograms of viral protein. This primary vaccination is followed two booster immunizations with 100 micrograms of viral protein delivered intramuscularly within the first year following primary immunization, followed by two booster immunizations with 500 micrograms of viral protein delivered intravaginally, intrarectally or intratracheally within the second year following primary immunization.

For gene therapy, sperm typically would be incubated with 100 micrograms of DNA, microvessels containing DNA, or engineered viral gene therapy delivery vectors, for 1 hour, after which they would be washed and administered by any of the above routes in vivo or added to target cells in vitro. For delivery of selected gene sequences to target cells via carriers combined with sperm membrane lysates or as components of molecular complexes containing sperm HLA-DR binding molecules, incubation of these formulations with 100 micrograms of nucleic acid would be followed by separation of the DNA/vesicle, DNA/lysate or DNA/molecular complexes from unattached DNA using any of several well-known chromatography procedures, followed by admission of the complex to patients by any of the routes described above.

Storage

The vaccine, contraceptive, and gene therapy formulations of the present invention preferably are stored with cryoprotectants in liquid nitrogen. Cryoprotectants are particularly important in those embodiments of the present invention in which live, inactivated sperm is used as an immunogen carrier. Any of a number of standard cryoprotectants can be used, such as the standard egg yolk formulations used by cryobanks for semen preservation. In those cases in which live, inactivated sperm is not used as the immunogen carrier, the stability of the vaccine and contraceptive preparations can vary according to the properties of the individual macromolecules that comprise the carrier. In addition, the stability of the vaccine, contraceptive and gene therapy preparations of the present invention can vary according to the properties of the immunogens and gene therapy carriers/constructs being used. For vaccine formulations to be administered prior to sexual contact (for delivery into mucosal cells by sperm after binding to live sperm in situ, or for positioning of immunogens for interaction with such cells simultaneously with their interaction with liver sperm after sexual contact), vaccine stability and storage conditions would be similar to those known for conventional vaccine formulations already in use in conventional and genital-mucosal formats. Typical ranges of stability for the vaccines and contraceptives of the present invention are approximately two months to five years.

Alternative Embodiments

Although this invention has been described in terms of certain embodiments, these embodiments are set forth for illustrative purposes and are not intended to limit the scope of the invention. It is apparent to those skilled in the art that various other modifications may be made to these embodiments without departing from the scope of the invention, which is properly determined upon reference to the following claims.

What is claimed is:

1. A composition, comprising:

a sperm cell carrier; and an antigen exogenous to said carrier.

2. The composition of claim 1, wherein said antigen is displayed on the surface of said carrier.

3. The composition of claim 1, wherein said antigen is incorporated into the nucleus of said carrier.

4. The composition of claim 1, wherein the antigen is selected from the group consisting of proteins, peptides, nucleic acids, lipids and carbohydrates.

5. The composition of claim 1, wherein said antigen is coupled to said carrier.

6. The composition of claim 1, further comprising an adjuvant.

7. The composition of claim 6, wherein the adjuvant is selected from the group consisting of BCG, *Brucella abortus,* and Cholera toxin B.

8. The composition of claim 1, wherein said antigen is particulate.

9. The composition of claim 8, wherein said antigen is selected from the group consisting of live attenuated bacteria, live attenuated viruses, inactivated bacteria, and inactivated viruses.

10. The composition of claim 8, wherein the antigen is selected from the group consisting of micelles, immune stimulating complexes (ISCOMS), liposomes, microspheres and lipid vesicles.

11. The composition of claim 1, wherein the antigen is obtained from an STD microbial pathogen.

12. The composition of claim 11, wherein said STD microbial pathogen is selected from the group consisting of *Chlamydia trachomatis, Hemophilus ducreyi, Neisseria gonorrhea,* and *Treponema pallidum.*

13. An in vitro method for identifying a vaccine immunogen, comprising the steps of:

isolating peripheral blood mononuclear cells (PBMCs) from an individual;

contacting said PBMCs with an antigen in the presence of a sperm cell carrier; and assaying proliferation of said PBMCs, wherein enhanced proliferation indicates that said antigen is a candidate vaccine immunogen.

14. The method of claim 13, wherein said assaying step comprises incorporation of tritiated thymidine.

15. The method of claim 13, wherein said antigen is coupled to said carrier.

16. The method of claim 13, wherein said antigen is obtained from an STD microbial pathogen.

17. The method of claim 13, additionally comprising contacting said PBMCs with said antigen in the absence of said sperm cell carrier and comparing the proliferation of said PBMCs in the presence and absence of said carrier, wherein enhanced PBMC proliferation in the presence of said carrier indicates that said antigen is a candidate vaccine immunogen.

* * * * *